(12) United States Patent  
Sasaki

(10) Patent No.: US 10,792,424 B2  
(45) Date of Patent: Oct. 6, 2020

(54) LIQUID MEDICINE ADMINISTRATION DEVICE

(71) Applicant: TERUMO KABUSHIKI KAISHA, Tokyo (JP)

(72) Inventor: Shohei Sasaki, Chigasaki (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 354 days.

(21) Appl. No.: 15/715,605

(22) Filed: Sep. 26, 2017

(65) Prior Publication Data

US 2018/0015222 A1 Jan. 18, 2018

Related U.S. Application Data

(63) Continuation of application No. PCT/JP2015/084949, filed on Dec. 14, 2015.

(30) Foreign Application Priority Data

Mar. 27, 2015 (JP) ................. 2015-067113

(51) Int. Cl.
*A61M 5/172* (2006.01)
*A61M 5/142* (2006.01)
(Continued)

(52) U.S. Cl.
CPC .......... *A61M 5/1723* (2013.01); *A61M 5/142* (2013.01); *A61M 5/1452* (2013.01);
(Continued)

(58) Field of Classification Search
None
See application file for complete search history.

(56) References Cited

U.S. PATENT DOCUMENTS

2009/0069784 A1 3/2009 Estes et al.
2009/0177142 A1 7/2009 Blomquist et al.
(Continued)

FOREIGN PATENT DOCUMENTS

JP 2002-523149 A 7/2002
WO WO-2009/081403 A2 7/2009

OTHER PUBLICATIONS

European Office Action in corresponding application No. 15887780.3.

(Continued)

*Primary Examiner* — Neil N Turk
(74) *Attorney, Agent, or Firm* — Foley & Lardner LLP

(57) ABSTRACT

A liquid medicine administration device for administration of a liquid medicine includes a liquid delivery unit; a control unit configured to control the liquid delivery unit; an activity detection unit; a storage unit configured to store data indicating an amount of the liquid medicine that has already been delivered into the living body; and a calculation unit configured to calculate a residual amount of the liquid medicine in the living body on the basis of (i) the data indicating the amount of the liquid medicine that has already been delivered by the liquid delivery unit into the living body, and (ii) the activity detected by the activity detection unit, and calculate a scheduled delivery amount of the liquid medicine to be administered into the living body on the basis of the residual amount of the liquid medicine.

4 Claims, 11 Drawing Sheets

(51) Int. Cl.
  *G16H 20/17* (2018.01)
  *G16H 20/30* (2018.01)
  *A61M 5/168* (2006.01)
  *A61M 5/145* (2006.01)
  *A61M 5/158* (2006.01)

(52) U.S. Cl.
  CPC .... *A61M 5/14216* (2013.01); *A61M 5/14248* (2013.01); *A61M 5/158* (2013.01); *A61M 5/168* (2013.01); *A61M 5/172* (2013.01); *G16H 20/17* (2018.01); *G16H 20/30* (2018.01); *A61M 2005/14268* (2013.01); *A61M 2005/1583* (2013.01); *A61M 2205/3379* (2013.01); *A61M 2205/3584* (2013.01); *A61M 2205/50* (2013.01); *A61M 2205/502* (2013.01); *A61M 2205/505* (2013.01); *A61M 2205/52* (2013.01); *A61M 2205/8206* (2013.01); *A61M 2230/201* (2013.01); *A61M 2230/63* (2013.01)

(56) References Cited

U.S. PATENT DOCUMENTS

2010/0286601 A1* 11/2010 Yodfat ................ G06F 19/3481
  604/66
2011/0105955 A1    5/2011 Yudovsky et al.

OTHER PUBLICATIONS

International Search Report issued in International Patent Application No. PCT/JP2015/084949, dated Mar. 8, 2016.
Office Action dated Nov. 5, 2019 in corresponding Chinese Application No. 201580072764.4.

\* cited by examiner

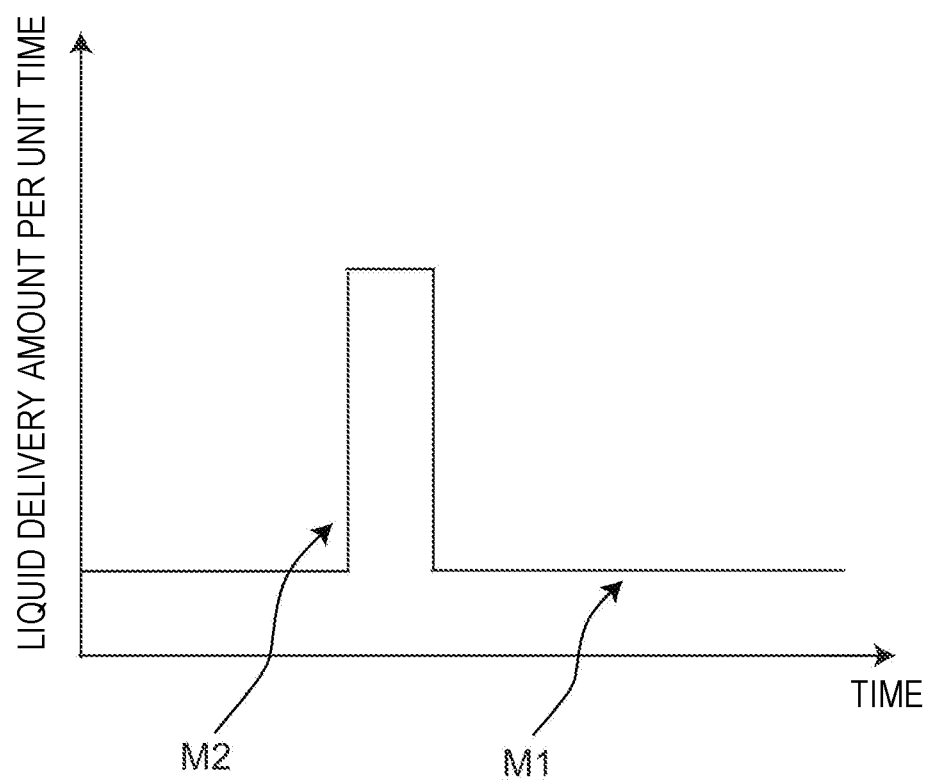

LIQUID MEDICINE ADMINISTRATION DEVICE

CROSS-REFERENCE TO RELATED APPLICATIONS

This application is a bypass continuation of PCT Application No. PCT/JP2015/084949, filed on Dec. 14, 2015, which claims priority to Japanese Application No. 2015-067113, filed on Mar. 27, 2015. The contents of these application are hereby incorporated by reference in their entireties.

BACKGROUND

As a device for administration of a liquid medicine such as insulin, a portable liquid medicine administration device for administration of the liquid medicine in a state in which the device is attached to skin of a user (patient, subject, or the like) to be an administration target is known.

In a case in which the liquid medicine is administered using the portable liquid medicine administration device, administration may be performed a plurality of times during a predetermined period with time intervals between each administration, depending on the user's daily routine or the like. In a case in which the administration is repeatedly performed a plurality of times in this way, when starting the administration, a liquid medicine previously administered may remain in a living body. When a liquid medicine is newly administered in a state where the liquid medicine remains in the living body, without considering a residual amount of the liquid medicine, there is a possibility that the liquid medicine is excessively administered into the living body.

In response to the problem as described above, JP 2002-523149 A discloses a liquid medicine administration device configured to estimate the residual amount of the liquid medicine in the living body on the basis of a dosage of the liquid medicine and an administration time of the liquid medicine, and deliver an appropriate dosage of the liquid medicine in consideration of the estimated residual amount.

SUMMARY

When the user performs an activity such as exercise after the administration of the liquid medicine and metabolism of the user temporarily increases, reactivity of the liquid medicine to an in-vivo substance may change in accordance with the increase in the metabolism, or an amount of the in-vivo substance may change due to a reaction different from a reaction with the liquid medicine. When the reactivity of the liquid medicine or the amount of the in-vivo substance increases, consumption of the liquid medicine administered into the living body is promoted, and when the reactivity of the liquid medicine or the amount of the in-vivo substance decreases, the consumption of the liquid medicine administered into the living body is suppressed. However, the conventional liquid medicine administration device as described above does not have a function of estimating the residual amount of the liquid medicine in the living body taking the activity such as exercise performed by the user after the administration of the liquid medicine into consideration. Therefore, in a case where the liquid medicine is newly administered after the user performed the activity such as exercise after the administration of the liquid medicine, an appropriate amount of the liquid medicine in consideration of the increase in the metabolism cannot be administered into the living body, which may cause underdosage in which the amount of the liquid medicine to be administered becomes smaller than a dosage actually required, or overdosage in which the amount of the liquid medicine to be administered becomes larger than the dosage actually required.

Therefore, an object of certain embodiments described in this application is to provide a liquid medicine administration device capable of estimating the residual amount of the liquid medicine in the living body of the user in consideration of the activity of the user, and administering the liquid medicine in an appropriate liquid delivery amount based on the residual amount.

In one embodiment, a liquid medicine administration device is provided for administering a liquid medicine in a state in which the device is attached to a body of a user. The device includes a liquid delivery unit configured to deliver the liquid medicine into a living body of the user, and a control unit configured to control liquid delivery operation of the liquid delivery unit. Further, the liquid medicine administration device includes an activity detection unit configured to detect an activity based on of a motion of the body of the user; a storage unit configured to store already-delivered liquid data relating to a delivery amount of the liquid medicine delivered by the liquid delivery unit into the living body; and a calculation unit configured to calculate a residual amount of the liquid medicine in the living body on the basis of the already-delivered liquid data stored by the storage unit and the activity detected by the activity detection unit, and calculate a scheduled delivery amount of the liquid medicine to be administered into the living body on the basis of the residual amount of the liquid medicine. The control unit controls the liquid delivery operation of the liquid delivery unit so that the scheduled delivery amount of the liquid medicine is delivered to the living body.

According to the liquid medicine administration device described above, the residual amount of the liquid medicine administered into the living body in advance is estimated on the basis of the activity of the user, and a scheduled delivery amount of the liquid medicine to be administered to the living body is administered into the living body on the basis of the residual amount. Therefore, a more appropriate amount of the liquid medicine can be administered into the living body.

BRIEF DESCRIPTION OF THE DRAWINGS

FIG. 5 exemplifies a liquid delivery mode of the liquid medicine administration device according to the embodiment.

DETAILED DESCRIPTION

Figure 1:
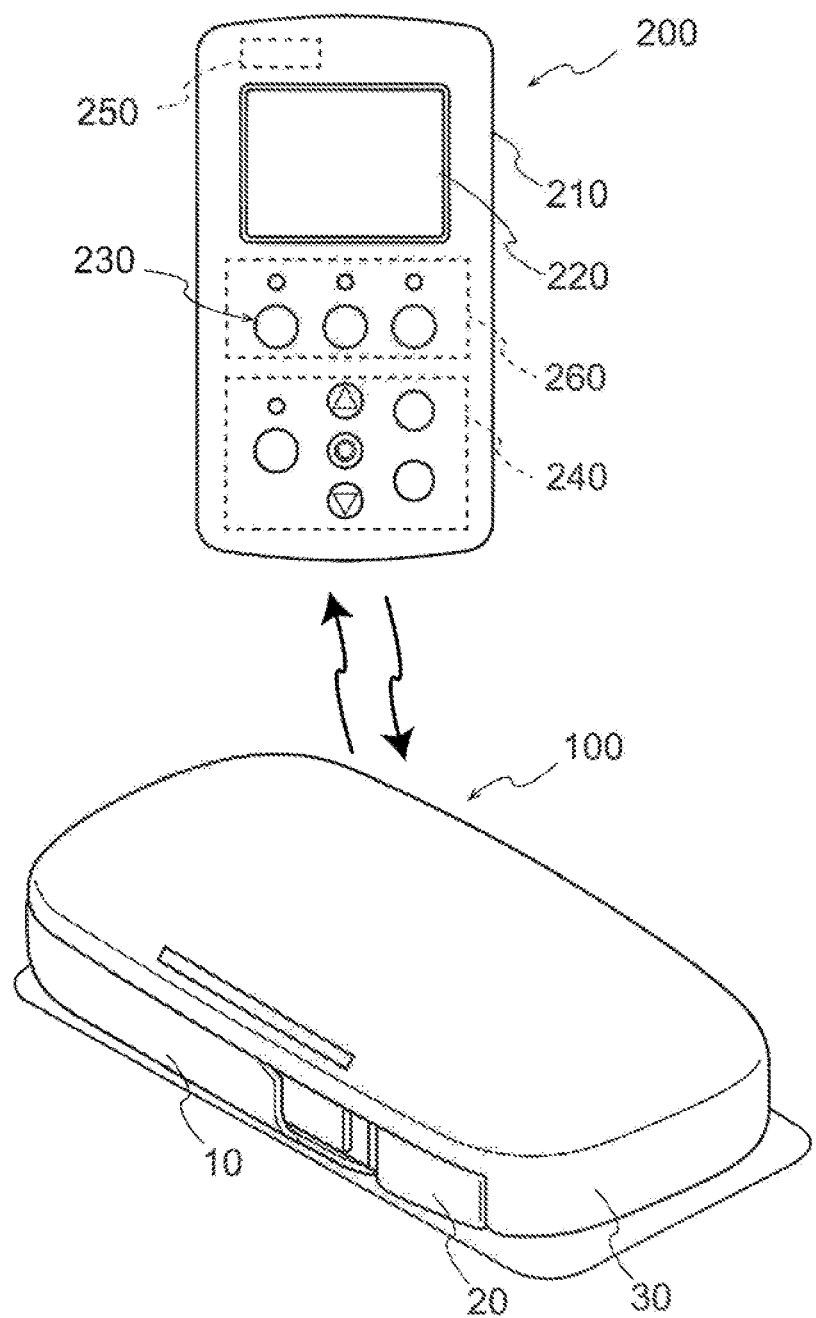
FIG. 1 is a schematic perspective view of a liquid medicine administration device according to an embodiment.

Hereinafter, embodiments of the present invention will be described with reference to accompanying drawings. A size or ratio of the members shown in the drawings may be exaggerated for convenience of explanation, and may be different from an actual size or an actual ratio.

Figure 6A:
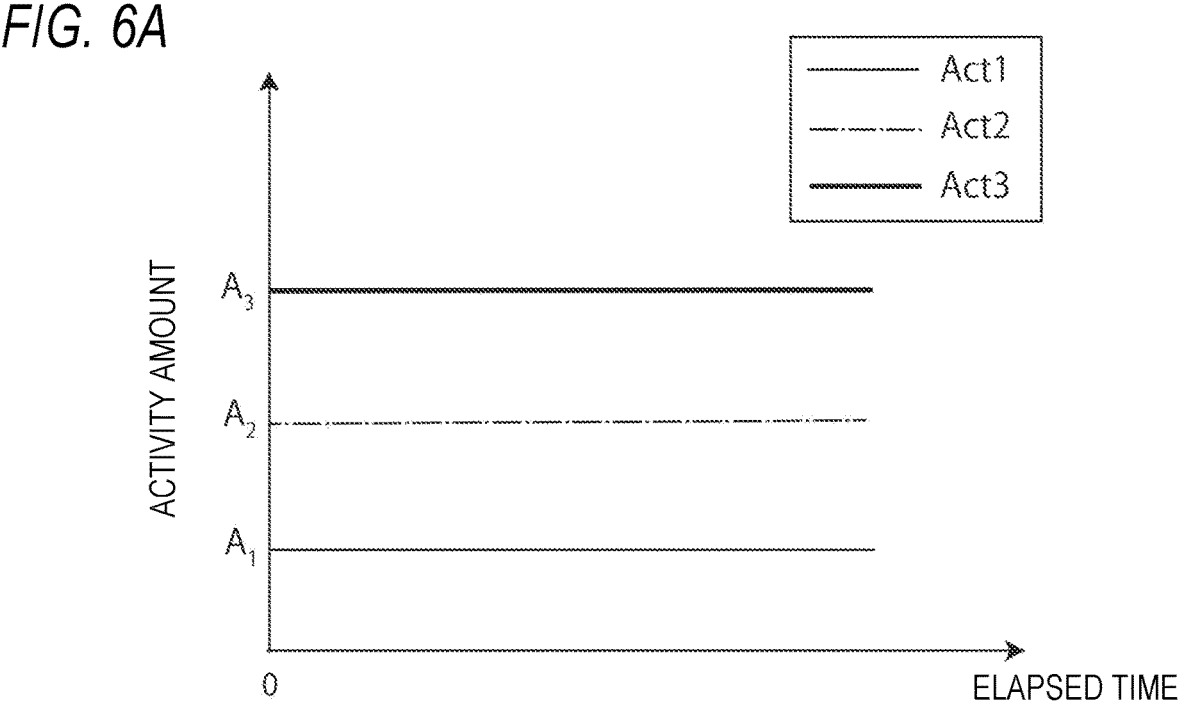
FIG. 6A illustrates temporal changes in activity amounts after administration of a liquid medicine according to the embodiment.
Figure 6B:
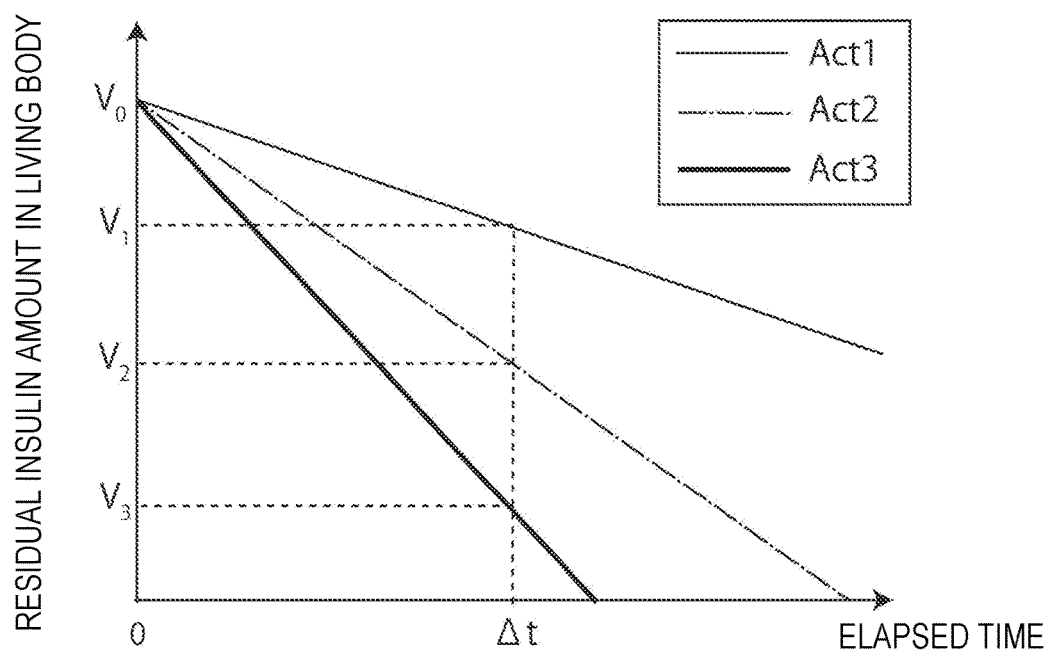
FIG. 6B illustrates temporal changes in residual amounts of the liquid medicine in the living body corresponding to each of the activity amounts in FIG. 6A.
Figure 7:
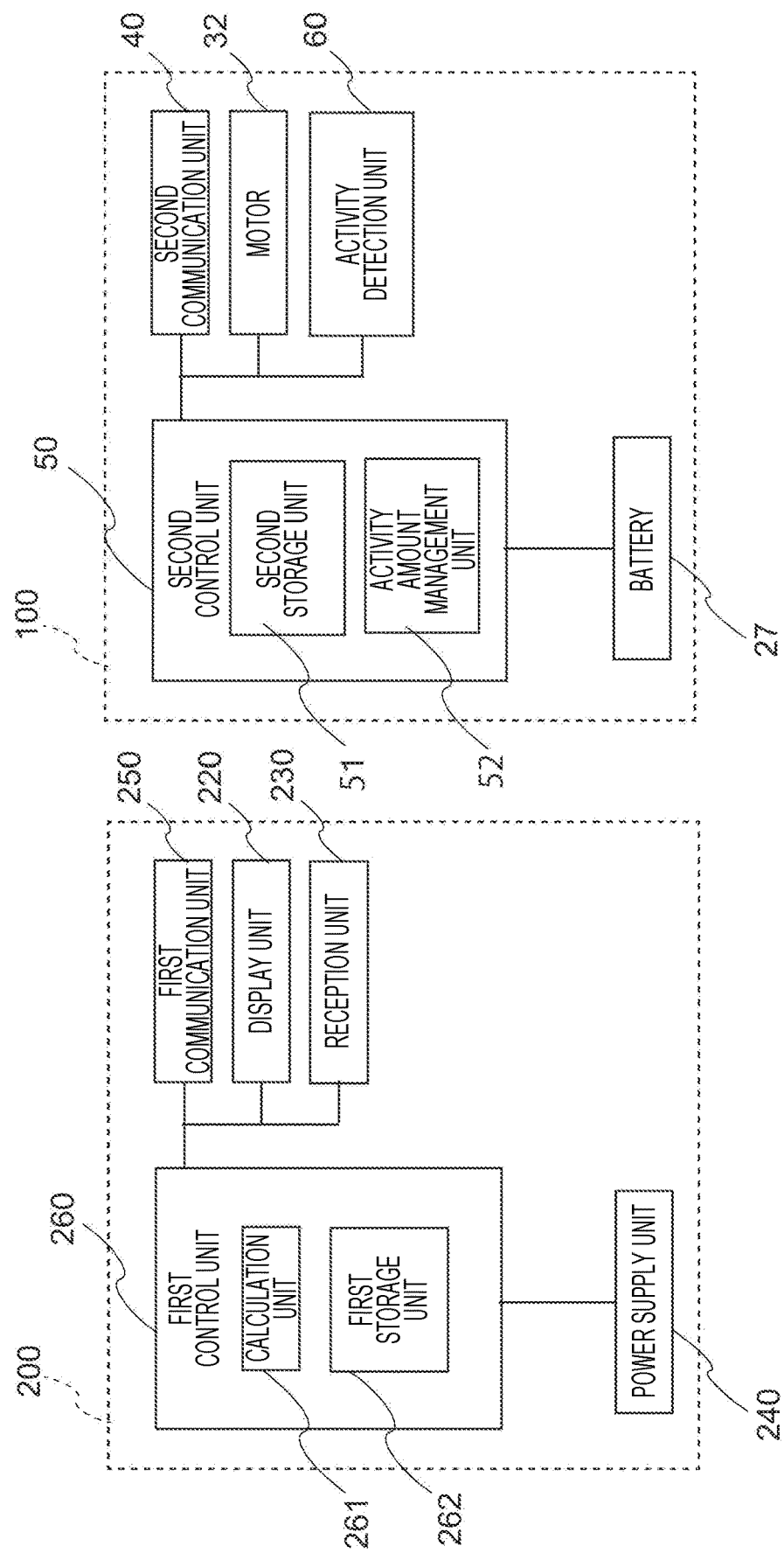
FIG. 7 is a block diagram illustrating an overall configuration of the liquid delivery unit and an overall configuration of a controller.
Figure 8A:
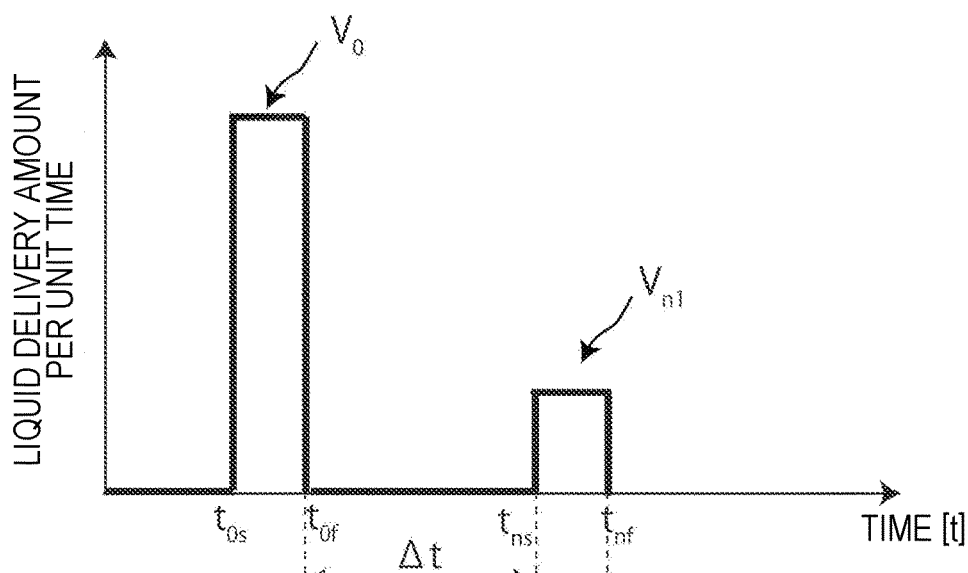
FIG. 8A illustrates a temporal change in a delivery amount of the liquid medicine according to the embodiment.
Figure 8B:
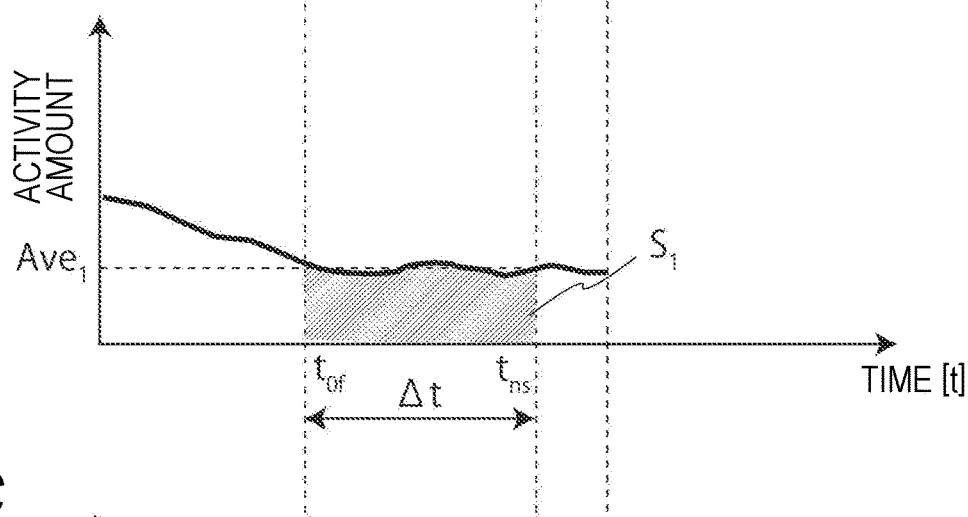
FIG. 8B illustrates a temporal change in an activity amount in FIG. 8A.
Figure 8C:
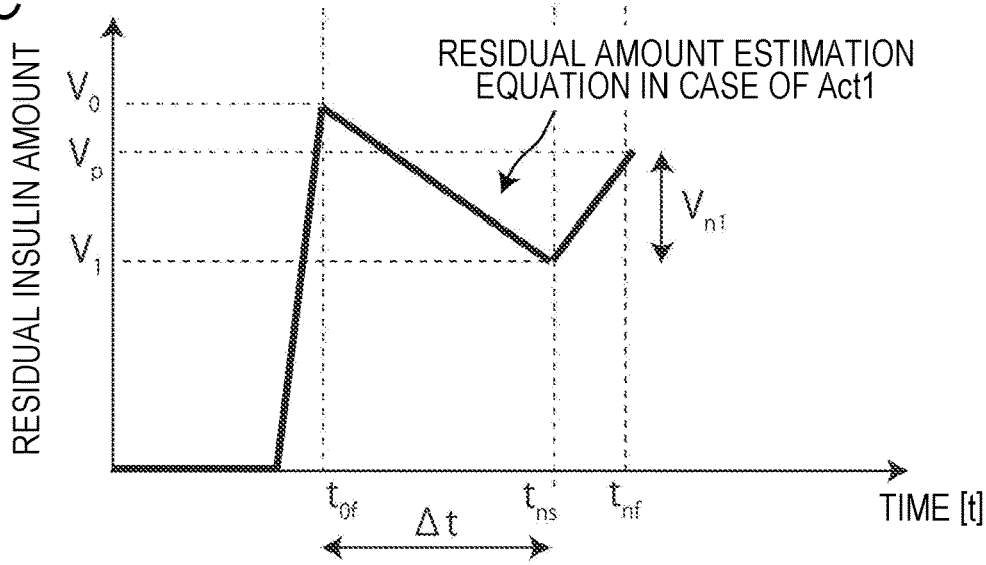
FIG. 8C illustrates a temporal change in a residual amount of the liquid medicine in FIG. 8A.
Figure 9A:
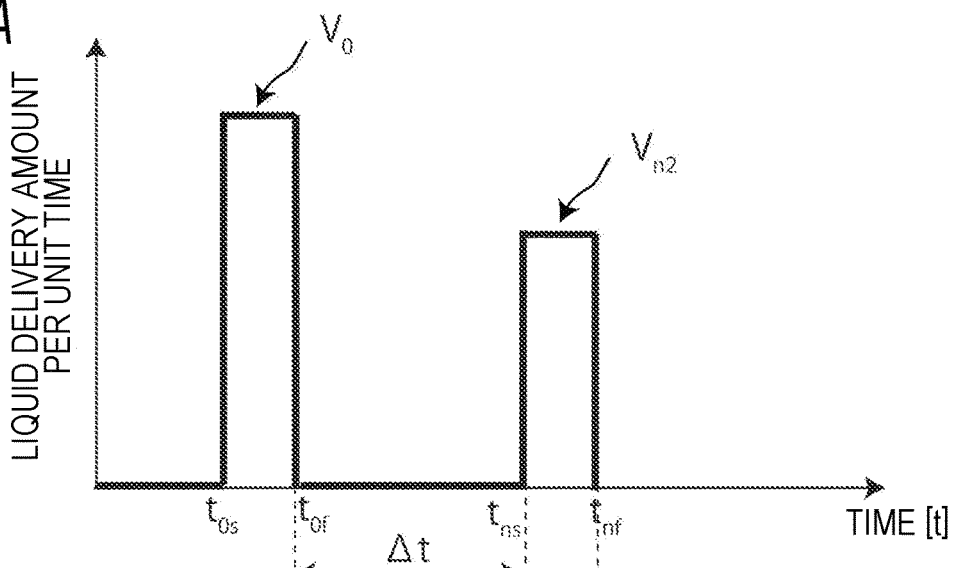
FIG. 9A illustrates a temporal change in a delivery amount of the liquid medicine according to the embodiment.
Figure 9B:
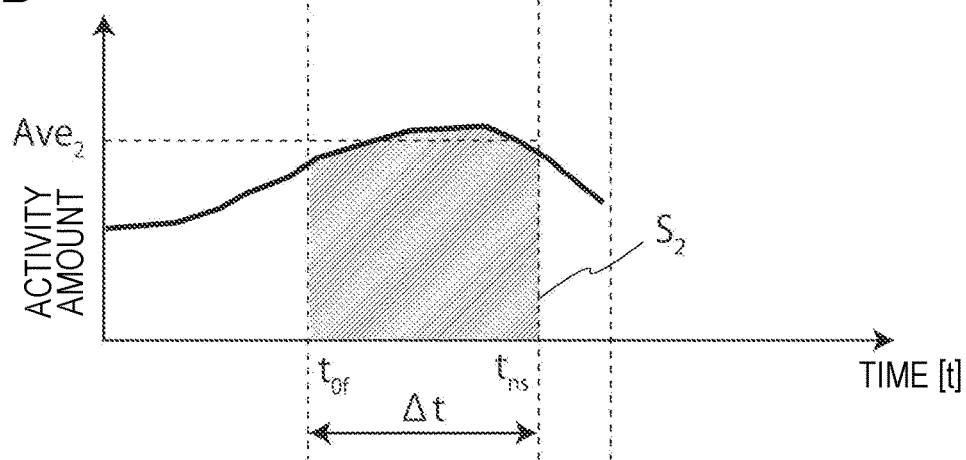
FIG. 9B illustrates a temporal change in an activity amount in FIG. 9A.
Figure 9C:
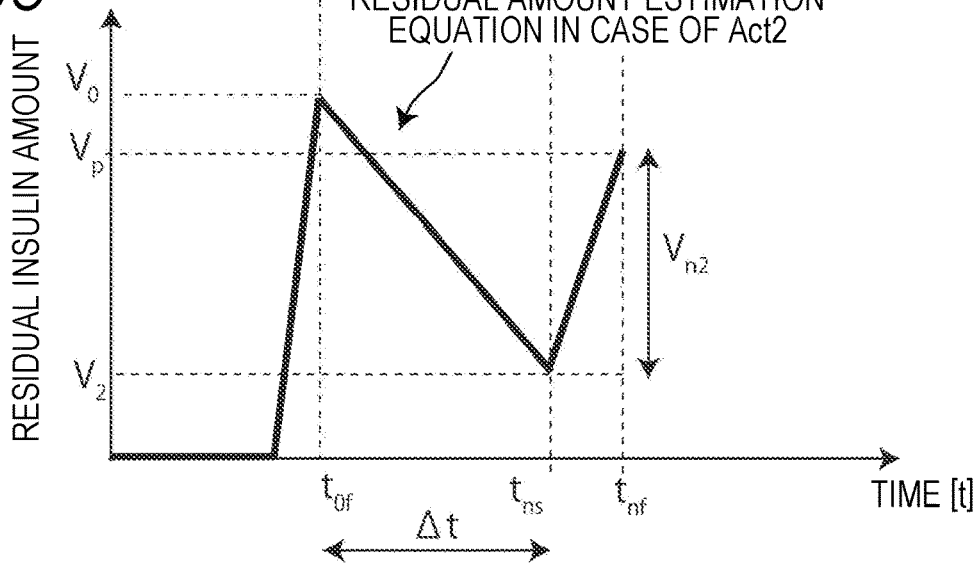
FIG. 9C illustrates a temporal change in a residual amount of the liquid medicine in FIG. 9A.
Figure 10:
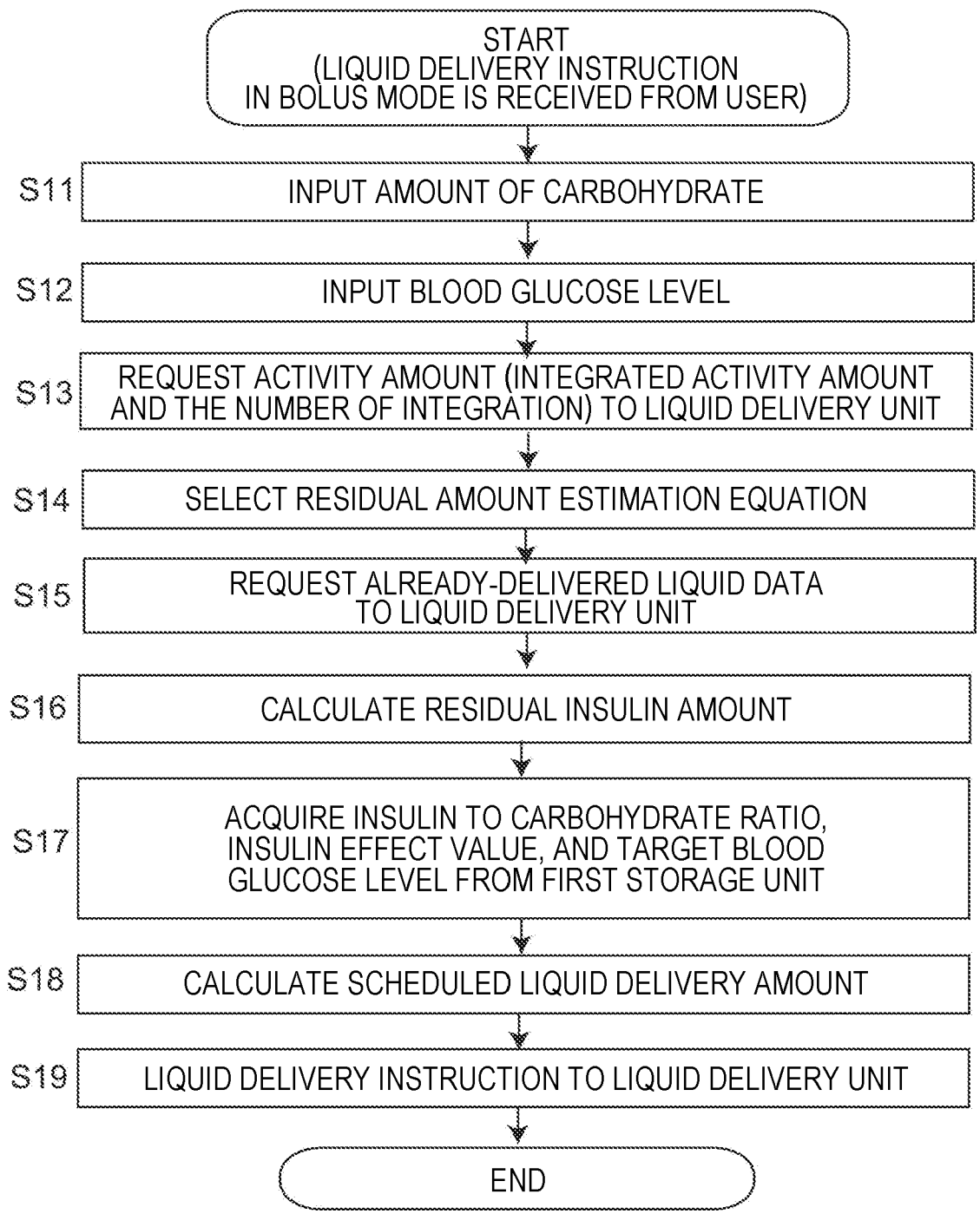
FIG. 10 is a flowchart of an operation process performed by the controller.
Figure 11:
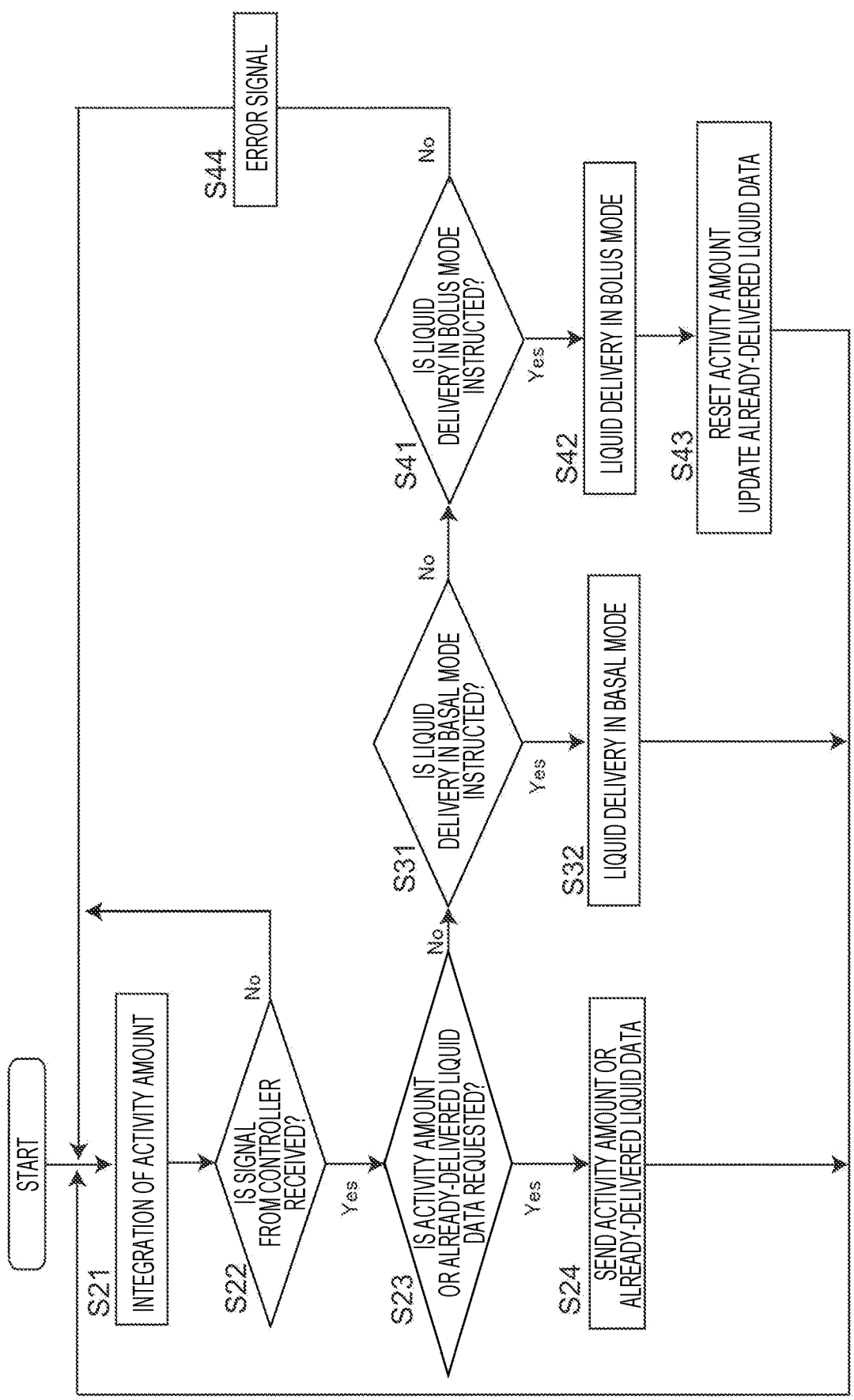
FIG. 11 is a flowchart of an operation process performed by the liquid delivery unit.

FIGS. 1 to 4B explains configurations of each unit of a liquid medicine administration device according to the embodiment, FIG. 5 explains a liquid delivery mode of the liquid medicine administration device, FIGS. 6A-6B explains a relationship between a residual amount of a liquid medicine and an activity amount, FIG. 7 is a block diagram illustrating an overall configuration of a liquid delivery unit and an overall configuration of a controller, FIGS. 8A-9C explain a method of calculating the residual amount of the liquid medicine in a living body and a scheduled liquid delivery amount, and FIGS. 10 and 11 explain an operation process of the liquid medicine administration device.

A liquid medicine administration device 300 according to the present embodiment is configured as a portable insulin administration device attached to a body of a diabetic patient as a user of the device to deliver insulin as a liquid medicine into the living body. In the following description, the liquid medicine administration device 300 is referred to as an insulin administration device 300.

As illustrated in FIG. 1, the insulin administration device 300 includes a liquid delivery unit 100 that performs liquid delivery operation to deliver insulin as the liquid medicine into the living body, and a controller 200 that provides various operation instructions to the liquid delivery unit 100.

The controller 200 includes a reception unit 230 capable of receiving instruction contents from the user, and sends a liquid delivery instruction to the liquid delivery unit 100 to deliver a predetermined amount of insulin based on the instruction contents. The user can, in a state where the liquid delivery unit 100 is attached to his/her body, provide the liquid delivery instruction to the liquid delivery unit 100 by operating the controller 200, which is separate from the liquid delivery unit 100.

First, an outline of the liquid delivery operation of the insulin administration device 300 will be described.

As illustrated in FIG. 5, the insulin administration device 300 is configured to be capable of performing, according to an instruction of the user, delivery in a basal mode in which insulin is delivered over time in a fixed amount (M1 in FIG. 5), and delivery in a bolus mode in which a delivery amount of insulin per unit time is temporarily increased (M2 in the drawing). The delivery in the bolus mode is generally performed immediately before or immediately after an activity that increases a blood glucose level (for example, ingestion of a meal). In addition, at a normal time, the delivery in the basal mode is performed so that an upper limit value and a lower limit value of the blood glucose level are maintained stably within a predetermined range.

In a case where insulin is administered in the bolus mode in which a large amount of insulin is administered periodically, insulin previously delivered in the bolus mode may remain in the living body. Therefore, when an amount of insulin to be delivered for administration of a more appropriate amount of insulin in the bolus mode (hereinafter referred to as a "scheduled liquid delivery amount") is determined, it is necessary to consider an amount of insulin remaining in the living body by the previous administration of insulin in the bolus mode (hereinafter referred to as a "residual insulin amount"). Further, a consumption amount of insulin changes when the user performs an activity such as exercise and the metabolism increases. Therefore, in order to administer a more appropriate amount of insulin, it is necessary to determine the residual insulin amount in consideration of the activity such as exercise by the user.

In delivery of insulin in the bolus mode, the insulin administration device 300 according to the present embodiment estimates the residual insulin amount on the basis of the activity corresponding to a motion of the body of the user, and determines the scheduled liquid delivery amount in consideration of the residual insulin amount.

Next, configurations of each unit in the insulin administration device 300 will be described in detail.

First, the liquid delivery unit 100 will be described.

Figure 2:
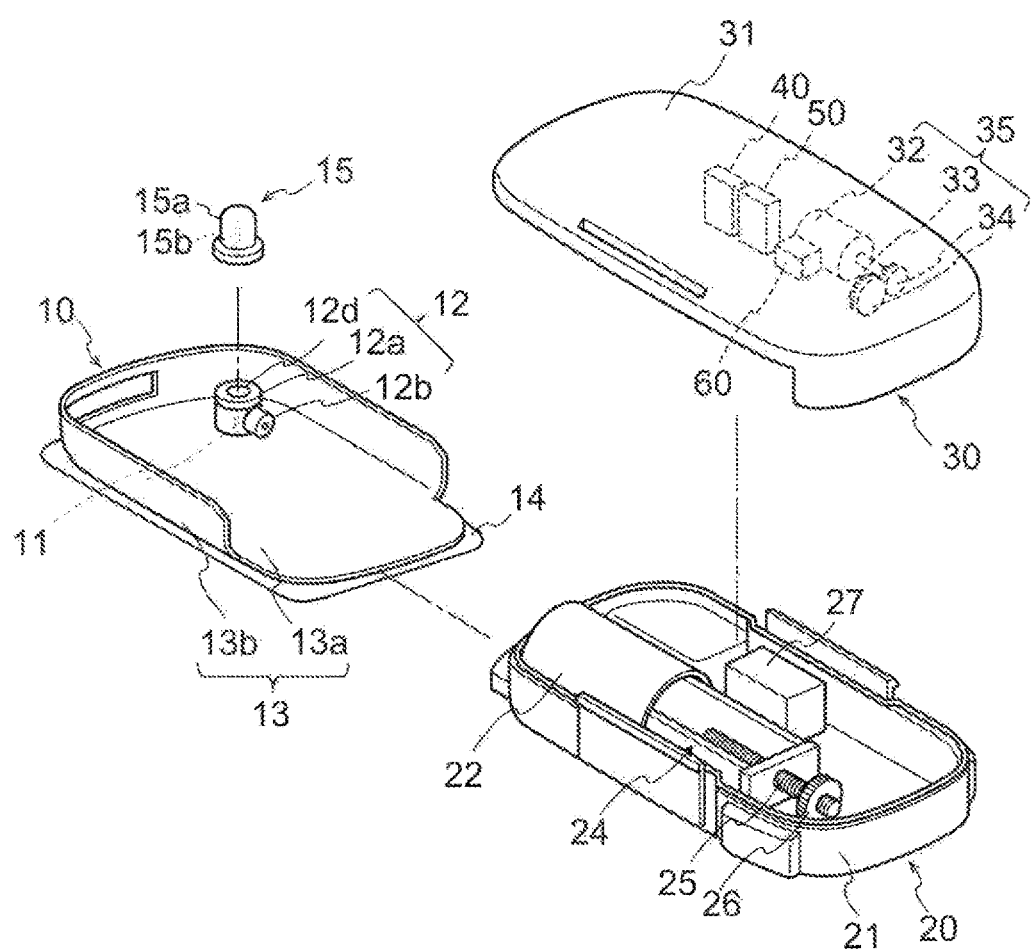
FIG. 2 is an exploded perspective view of a liquid delivery unit provided in the liquid medicine administration device according to the embodiment.

As illustrated in FIG. 2, the liquid delivery unit 100 is attached to the body of the user, and includes an injection unit 10 including a cannula 11 to be indwelled in the living body of the user, and the like, a disposable liquid delivery disposable unit 20 configured to be connectable/separable to/from the injection unit 10 and include a syringe 22 filled with insulin, and the like, and a reusable liquid delivery reusable unit 30 configured to be connectable/separable to/from the liquid delivery disposable unit 20 and include a drive unit 35 that drives liquid delivery operation, and the like. In a case where the insulin in the syringe 22 becomes empty, for example, the insulin administration device 300 itself can be repeatedly used by replacing the liquid delivery disposable unit 20 with a new one as necessary.

The injection unit 10 will be described.

As illustrated in FIG. 2, the injection unit 10 includes the cannula 11, a support member 12 that supports the cannula 11, an injection unit holding member (cradle) 13 that includes a flat plate-like placing part 13a and a vertical wall part 13b projecting from a part of an outer peripheral edge portion of the placing part 13a, and an attachment part 14 that is provided on a rear surface side of the injection unit holding member 13 and attaches the injection unit 10 to the body of the user.

The injection unit holding member 13 is provided with an engagement part (not illustrated) that maintains mechanical connection with the liquid delivery disposable unit 20. The engagement part can be constituted by a projection, a recess, or the like which can be freely fitted to a projection, a recess, or the like which is formed on a side of the liquid delivery disposable unit 20, for example. As illustrated in FIGS. 3B and 3C, the placing part 13a of the injection unit holding member 13 is provided with an insertion hole 13c through which the cannula 11 can be inserted.

As illustrated in FIG. 2, the support member 12 includes a main body part 12a formed in a substantially cylindrical shape. Further, the main body part 12a is provided with a connection part 12b to which a liquid delivery tube 23 (see FIG. 4B) provided in the liquid delivery disposable unit 20 is connected.

As illustrated in FIGS. 3B and 3C, the cannula 11 is provided to freely project from a bottom surface of the main body part 12a. In the main body part 12a, a flow path 12c that communicates the connection part 12b and an internal flow path (lumen) of the cannula 11 when the cannula 11 is projected from the main body part 12a is provided. Note that FIGS. 3B and 3C schematically illustrate states before and after the cannula 11 is projected from the main body part 12a.

The attachment part 14 is formed of a substantially rectangular sheet-like member. In the attachment part 14, adhesiveness is imparted to a surface (rear surface) opposite to a surface which is arranged to face the rear surface of the injection unit holding member 13. The injection unit 10 can be attached to the body of the user by using the adhesiveness of the attachment part 14. Note that detachable release paper or the like that covers and protects the attachment part 14 may be used to prevent the attachment part 14 from being attached unintentionally.

An example of operation when the cannula 11 housed in the main body part 12a of the support member 12 is introduced into the living body of the user will be described.

When using the insulin administration device 300, the user attaches the injection unit 10 to his/her body (skin surface) via the attachment part 14. At this point, the cannula 11 is housed in the main body part 12a. The cannula 11 is projected from the main body part 12a toward inside of the living body of the user by using a puncture tool 15 which is an exclusive tool used for introduction into the living body.

Figure 3A:
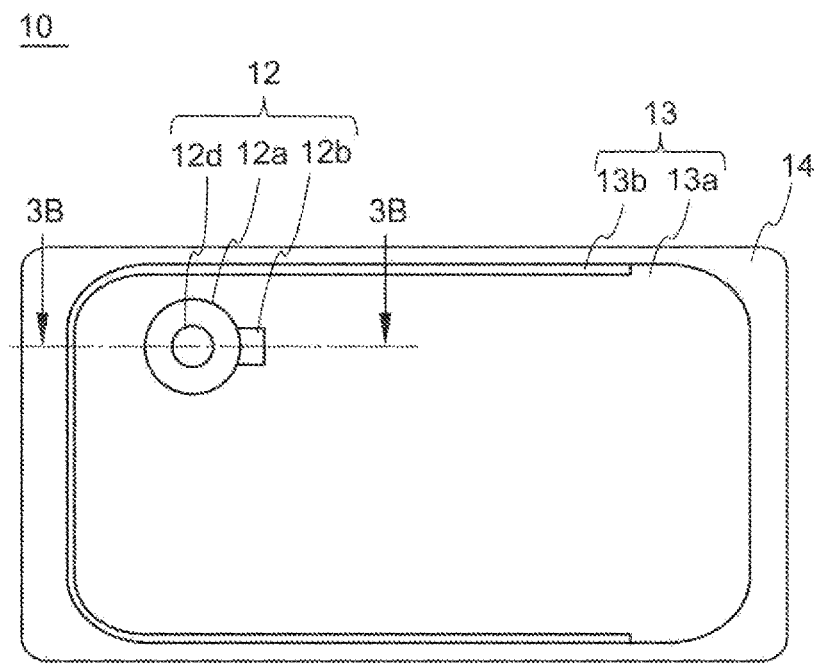
FIG. 3A is a top view of an injection unit provided in the liquid delivery unit.
Figure 3B:
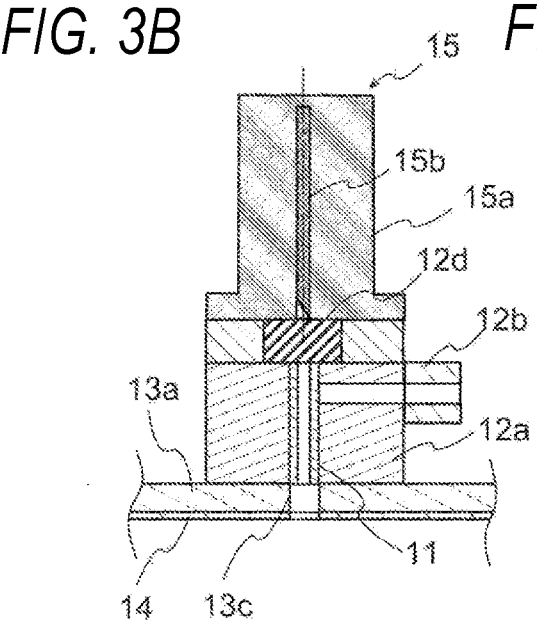
FIGS. 3B and 3C are cross-sectional views taken along a line 3B-3B of FIG. 3A, illustrating an operation when a cannula is introduced into a living body using a puncture tool.
Figure 3C:
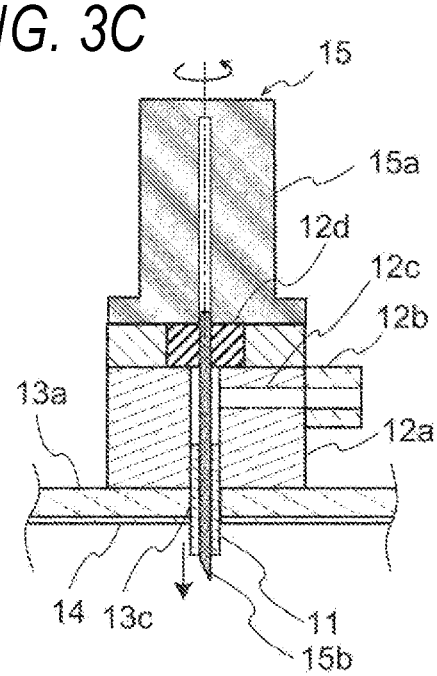

As illustrated in FIGS. 2 and 3 B, the puncture tool 15 includes a grip part 15a which can be gripped by the user with fingers, and a puncture needle 15b having a sharp needle point. When the puncture tool 15 is in an unused state, the puncture needle 15b is housed inside the grip part 15a.

When the puncture tool 15 is attached to an upper surface portion of the main body part 12a, and the puncture tool 15 is rotated with respect to the main body part 12a, as illustrated in FIG. 3B, the puncture needle 15b is inserted through the lumen of the cannula 11, and projects from a lower surface side (rear surface side) of the main body part 12a together with the cannula 11, as illustrated in FIG. 3C.

Portions of the puncture needle 15b and the cannula 11 which project from the main body part 12a penetrate surface skin of the living body through the insertion hole 13c and are introduced into the living body. After confirming that the puncture needle 15b and the cannula 11 are introduced into the living body, the grip part 15a is lifted up and the puncture needle 15b is pulled out from the cannula 11. As a result of this operation, the cannula 11 is indwelled in the living body with the puncture needle 15b pulled out (see FIG. 4B).

As illustrated in FIG. 2, the liquid delivery disposable unit 20 and the liquid delivery reusable unit 30 can be attached to the injection unit 10 after the puncture tool 15 is removed. Note that a sealant 12d made of an elastic material or the like is provided at a portion through which the puncture needle 15b is inserted on the upper surface portion of the main body part 12a so that sealing property with external parts is ensured even after the puncture needle 15b is removed.

Figure 4A:
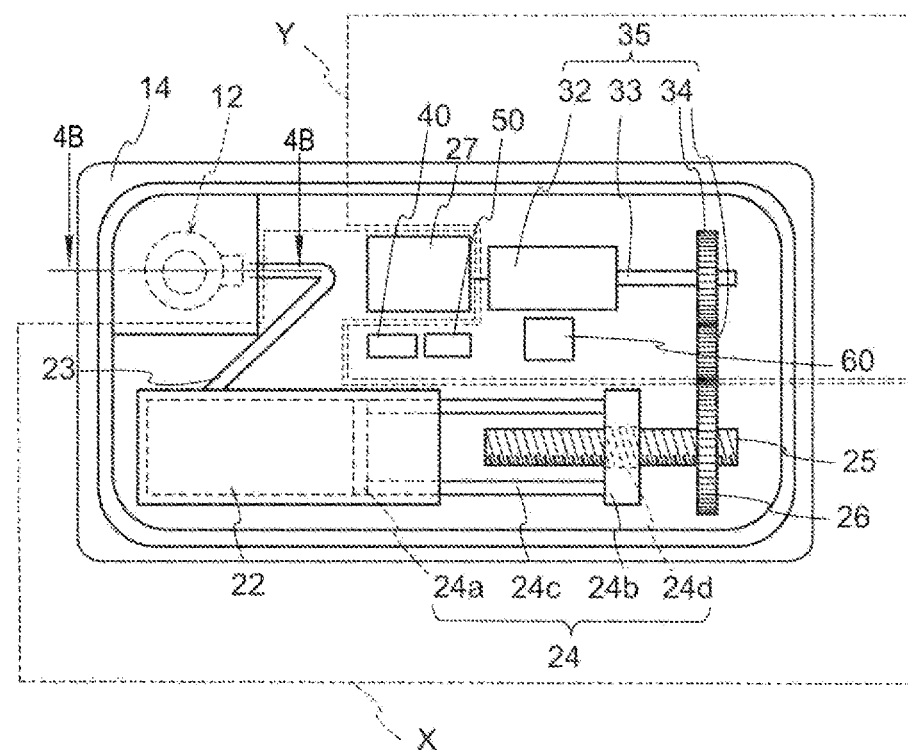
FIG. 4A is a plan view schematically illustrating a structure of each unit in the liquid delivery unit.

Next, the liquid delivery disposable unit 20 and the liquid delivery reusable unit 30 will be described. Note that FIG. 4A illustrates the liquid delivery unit 100 in a state where the injection unit 10, the liquid delivery disposable unit 20, and the liquid delivery reusable unit 30 are connected. A portion surrounded by a broken line X is housed in the liquid delivery disposable unit 20, and a portion surrounded by a broken line Y is housed in the liquid delivery reusable unit 30.

As illustrated in FIGS. 2 and 4A, the liquid delivery disposable unit 20 includes a liquid delivery disposable unit holding member 21 placed on the injection unit holding member 13, the syringe 22 filled with insulin, and the liquid delivery tube 23 that communicates the connection part 12b provided in the injection unit 10 and the syringe 22.

The liquid delivery disposable unit 20 further includes a pusher 24 that slides in the syringe 22 to deliver insulin in the syringe 22 to the liquid delivery tube 23, a feed screw 25 that meshes with a female screw part 24d formed in the pusher 24 to feed the pusher 24 into the syringe 22, a gear 26 that transmits rotational force from the drive unit 35 of the liquid delivery reusable unit 30 to the feed screw 25, and a battery 27 that supplies electric power to the drive unit 35 and the like.

As illustrated in FIG. 4A, the pusher 24 includes a push plate 24a that slides in the syringe 22 while maintaining sealing property, a feed plate 24b having the female screw part 24d, and a connecting plate 24c connected to the push plate 24a and the feed plate 24b.

A part of the feed screw 25 is meshed with the female screw part 24d of the feed plate 24b. Further, a base end portion of the feed screw 25 is fixed to the gear 26. When the feed screw 25 rotates with rotation of the gear 26, the feed plate 24b moves on the feed screw 25. The push plate 24a connected to the feed plate 24b via the connecting plate 24c slides in the syringe 22 with the movement of the feed plate 24b.

Figure 4B:
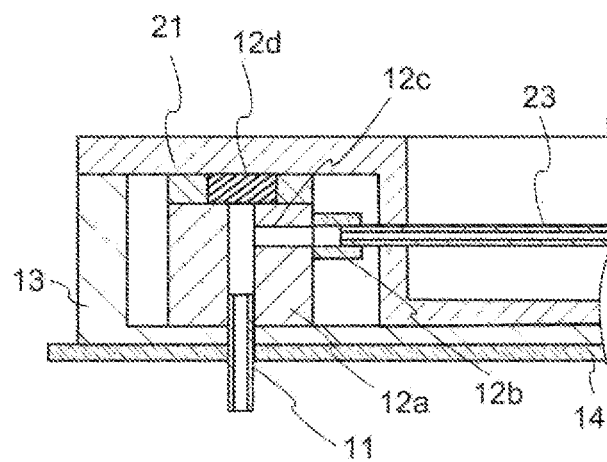
FIG. 4B is a cross-sectional view taken along a line 4B-4B of FIG. 4A.

The liquid delivery tube 23 is constituted by a metallic thin tube that extends from the inside of the syringe 22 toward the connection part 12b of the cannula 11. When the liquid delivery disposable unit holding member 21 is connected to the injection unit holding member 13 while sliding the liquid delivery disposable unit holding member 21, as illustrated in FIG. 2, a tip of the liquid delivery tube 23 is inserted into the connection part 12b of the injection unit 10, as illustrated in FIG. 4B. The sealant (not illustrated) made of an elastic member or the like is provided at a portion of the connection part 12b through which the liquid delivery tube 23 is inserted. With this configuration, the connection part 12b and the liquid delivery tube 23 can be liquid-tightly connected.

The battery 27 is electrically connected to the drive unit 35 (a motor 32) in the liquid delivery reusable unit 30 when the liquid delivery disposable unit 20 is connected to the liquid delivery reusable unit 30. With this configuration, electric power can be supplied from the battery 27 to the drive unit 35. Further, the battery 27 is also electrically connected to a second communication unit 40 and a second control unit 50 that are housed in the liquid delivery reusable unit 30, and supplies electric power to each of the second communication unit 40 and the second control unit 50.

As illustrated in FIGS. 2 and 4A, the liquid delivery reusable unit 30 includes a liquid delivery reusable unit holding member 31 connected to the liquid delivery disposable unit holding member 21, the motor 32 electrically connected to the battery 27, a rotary shaft 33 rotatably driven by the motor 32, a plurality of gears 34 that transmits the rotation of the rotary shaft 33 to the feed screw 25, and an activity detection unit 60 that detects an activity based on a motion of the body of the user. Note that the drive unit 35 that drives liquid delivery operation of the liquid delivery unit 100 is configured by the motor 32, the rotary shaft 33, and the gears 34.

As illustrated in FIG. 2, the liquid delivery reusable unit holding member 31 is configured as a case (housing) that covers the liquid delivery disposable unit holding member 21. Each of constituent members of the above-described liquid delivery reusable unit 30 is housed inside the liquid delivery disposable unit holding member 21.

As illustrated in FIG. 4A, the motor 32 is disposed at a position where the motor 32 can be electrically connected to the battery 27 of the liquid delivery disposable unit 20 when the liquid delivery reusable unit 30 is connected to the liquid delivery disposable unit 20. The plurality of gears 34 include a first gear connected to the rotary shaft 33 of the motor 32, a second gear meshed with the gear 26 provided in the liquid delivery disposable unit 20, and a third gear disposed between the first and second gears and meshed with each of the gears. Note that, in the present embodiment, the gears 34 are exemplified as gears configured by the first and second gears, for simplification.

The activity detection unit 60 is an example of an activity detection unit that detects an activity based on the motion of the body of the user, and constituted by an acceleration sensor that detects the amount of the motion (acceleration in the motion, and the like) when the user moves each part of the body as an activity amount. As the acceleration sensor, for example, a known sensor such as a piezoelectric element or a conductive element can be used. Note that the configuration of the activity detection unit 60 is not particularly limited as long as the activity detection unit 60 can detect an activity corresponding to the motion of the body of the user, and the activity detection unit 60 may be configured by an angular velocity sensor or a vibration sensor, for example. Further, the activity detection unit may also be configured to detect the activity on the basis of a time interval of the motion of the body of the user, the number of steps, a travel distance, calorie consumption, and the like.

Next, a method of attaching the liquid delivery disposable unit 20 and the liquid delivery reusable unit 30 to the injection unit 10 will be described.

When using the insulin administration device 300, the user connects and integrates the liquid delivery disposable unit 20 and the liquid delivery reusable unit 30. Then, in a state where the cannula 11 is indwelled in the living body, the user connects the liquid delivery disposable unit 20 and the liquid delivery reusable unit 30 that are integrated to the injection unit 10 attached to the body of the user.

Note that, before connecting the liquid delivery disposable unit 20 and the liquid delivery reusable unit 30 that are integrated to the injection unit 10, the user performs priming for filling insulin in the liquid delivery tube 23 of the liquid delivery disposable unit 20. Specifically, by operating the drive unit 35 and moving the pusher 24 by a predetermined amount, the insulin contained in the syringe 22 is sent to the liquid delivery tube 23 so that the insulin is filled in the liquid delivery tube 23. By performing the priming, it is possible to remove air in the liquid delivery tube 23 in advance and then deliver the liquid into the living body. Therefore, it is possible to prevent air from being entered when the insulin is delivered into the living body, and to deliver a more accurate amount of the insulin.

Next, the controller 200 will be described.

As illustrated in FIG. 1, the controller 200 includes a controller main body unit 210, a display unit 220 provided in the controller main body unit 210, the reception unit 230 capable of receiving instruction contents from the user, and a power supply unit 240 that supplies electric power to each unit of the controller 200.

The display unit 220 can be constituted by, for example, a liquid crystal display. The display unit 220 can display information necessary for the user to operate the insulin administration device 300, a progress status of the liquid delivery operation, and the like.

The reception unit 230 has a plurality of buttons, and receives the instruction contents from the user by operation of the buttons. The reception unit 230 is provided with, for example, a button for selecting the basal mode, the bolus mode, priming operation, or the like, and a button for switching display contents of the display unit 220. The user can perform transmission of a liquid delivery instruction, selection of a liquid delivery mode, designation of various operations, and the like by selecting and pressing these buttons according to the purpose.

Next, with reference to FIGS. 1 and 4A, a control system and a communication function of the controller 200 and the liquid delivery unit 100 will be described.

As illustrated in FIG. 1, the controller 200 includes a first communication unit 250 capable of wirelessly communicating with the liquid delivery unit 100, and a first control unit 260 that integrally controls the insulin administration device 300.

As illustrated in FIG. 4A, the liquid delivery reusable unit 30 of the liquid delivery unit 100 includes the second communication unit 40 capable of wirelessly communicating with the controller 200, and the second control unit 50 that integrally controls operation of the liquid delivery unit 100 in response to an instruction from the first control unit 260.

The first communication unit 250 of the controller 200 and the second communication unit 40 of the liquid delivery unit 100 can transmit/receive information to/from each other using Bluetooth Low Energy (BLE) communication, which is a short-range wireless communication technology, enabling communication with low electric power.

The first control unit 260 of the controller 200 and the second control unit 50 of the liquid delivery unit 100 are configured by known microcomputers including a CPU, a RAM, and a ROM. The CPU provided in each of the first control unit 260 and the second control unit 50 reads out various programs stored in the ROM in advance to the RAM and executes the programs, so that predetermined operation control to be described later is executed.

The above is the configurations of each unit of the insulin administration device 300.

Next, a function of the insulin administration device 300 will be described.

The insulin administration device 300 calculates a scheduled delivery amount of insulin in the bolus mode on the basis of Equation 1 below.

[Mathematical Formula 1]

$$\text{Schduled liquid delivery amount} = \frac{\text{Amount of carbohydrate}}{\text{Insulin to carbohydrate ratio}} + \frac{\text{Measured blood glucose level} - \text{Target blood glucose level}}{\text{Insulin effect value}} - \text{Residual Insulin amount} \quad \text{(Equation 1)}$$

In the above Equation 1, the amount of carbohydrate [g] is an amount of carbohydrate taken by the user in a meal immediately before start of liquid delivery in the bolus mode. The insulin to carbohydrate ratio [g/unit] is an amount of insulin that can treat 1 g of carbohydrate and is a predetermined value determined for each user. The measured blood glucose level [mg/dL] is a blood glucose level measured before the user takes a meal. The target blood glucose level [mg/dL] is a blood glucose level to be a target of adjustment by administration of insulin. The insulin effect value [mg/dL/unit] is a blood glucose level which decreases when one unit of insulin is administered, and is a predetermined value determined for each user.

In the above Equation 1, the residual insulin amount [unit] is the amount of insulin which is remaining in the living body as a result of the administration at the time of the previous liquid delivery in the bolus mode (hereinafter referred to as a "previous bolus"). As described above, in the calculation of the residual insulin amount, the activity amount associated with the motion of the body of the user is taken into consideration. A method of calculating the residual insulin amount taking the activity amount into consideration will be described with reference to FIGS. 6A-6B illustrating a relationship between the activity amount and the residual insulin amount.

FIG. 6A illustrates temporal changes in the activity amounts, in which a vertical axis indicates the activity amount detected by the activity detection unit 60, and a horizontal axis indicates an elapsed time from the previous bolus. In FIG. 6A, three motion patterns are exemplified, specifically, a motion pattern of Act1 (thin line) in a case where the amount of the motion of the body of the user was relatively small since the user had a sleep or a rest continuously, and accordingly, a constant small activity amount A1 was detected, a motion pattern of Act2 (dashed line) in a case where the user continuously performed daily activities such as walking, and accordingly, a moderate activity amount A2 was detected, and a motion pattern of Act3 (thick line) in a case where the user continuously performed a certain relatively vigorous exercise such as sports, and accordingly, a constant large activity amount A3 was detected.

FIG. 6B illustrates temporal changes in the residual insulin amounts corresponding to each of the three motion patterns Act1, Act2, and Act3 illustrated in FIG. 6A, in which a vertical axis indicates the residual insulin amount, and a horizontal axis indicates an elapsed time from the previous bolus. As illustrated in FIG. 6B, as the activity amount of the user increases, consumption of insulin is promoted and a decreasing rate of the residual insulin amount becomes higher. For example, in FIG. 6B, when a time $\Delta t$ elapses from administration of $V_0$ of insulin in the previous bolus, the residual insulin amounts becomes $V_1$ in the case of Act1, $V_2$ in the case of Act2, and $V_3$ in the case of Act3. In other words, the larger the activity amount is, the smaller the residual insulin amount after a predetermined time elapses becomes. In this manner, the residual insulin amount can be estimated on the basis of the liquid delivery amount in the previous bolus, the elapsed time from the previous bolus, and the activity amount after the previous bolus.

Note that, in the present embodiment, for simplicity of description, it is assumed that insulin administered into the living body decreases at a constant rate with a lapse of time, as illustrated in FIG. 6B. It is also assumed that a linear relationship (a relationship of a linear function) holds between the residual insulin amount and the elapsed time from the previous bolus, and that the residual insulin amount can be calculated using a residual amount estimation equation (Equation 2 below) for calculation of the residual insulin amount on the basis of the liquid delivery amount in the previous bolus, and the elapsed time and the activity amount from the previous bolus.

[Mathematical Formula 2]

Residual insulin amount=Liquid delivery amount at previous bolus−Insulin consumption rate× Elapsed time from the previous bolus    (Equation 2)

In the above Equation 2, the insulin consumption rate [unit/hour] is a consumption amount of insulin per unit time in the living body. The insulin consumption rate is a predetermined value corresponding to the activity amount after the previous bolus.

The calculation of the scheduled liquid delivery amount and the residual insulin amount shown in the above Equations 1 and 2 is performed using each function of the first control unit 260 provided in the controller 200, and the second control unit 50 provided in the liquid delivery unit 100.

Hereinafter, each function of the first control unit 260 and the second control unit 50 will be described with reference to a block diagram of the liquid delivery unit 100 and the controller 200 illustrated in FIG. 7.

The second control unit 50 provided in the liquid delivery unit 100 is connected to the second communication unit 40, the motor 32, the activity detection unit 60, and the battery 27, and integrally controls operation thereof. Further, the second control unit 50 has functions as a second storage unit 51 that stores already-delivered liquid data relating to an delivery amount of insulin that has already been delivered by the liquid delivery unit 100 into the living body in the bolus mode, and an activity amount management unit 52 that manages the activity amount detected by the activity detection unit 60.

The "already-delivered liquid data" includes the delivery amount of insulin by the liquid delivery unit 100 and a delivery end time of insulin in the previous bolus. The second control unit 50 acquires the liquid delivery amount and the liquid delivery end time from a drive signal of the motor 32 provided in the liquid delivery unit 100 every time the liquid delivery is performed in the bolus mode by the liquid delivery unit 100. The second storage unit 51 then updates the acquired liquid delivery amount and liquid delivery end time as the already-delivered liquid data.

The activity amount management unit 52 periodically acquires the activity amount from the activity detection unit 60. The activity amount management unit 52 then integrates the acquired activity amount between completion of the liquid delivery operation in the bolus mode by the liquid delivery unit 100 and start of another liquid delivery operation (liquid delivery in the next bolus mode). The activity amount management unit 52 also counts the number of integration at this time.

The first control unit 260 provided in the controller 200 is connected to the first communication unit 250, the display unit 220, the reception unit 230, and the power supply unit 240, and integrally controls operation thereof.

Further, the first control unit 260 has functions as a calculation unit 261 that calculates the residual insulin amount on the basis of the already-delivered liquid data stored by the second storage unit 51 and the activity amount detected by the activity detection unit 60, and calculates the scheduled delivery amount of insulin to be administered to the living body on the basis of the residual insulin amount, and a first storage unit 262 that stores various pieces of information necessary for calculation by the calculation unit 261. In addition, the first control unit 260 and the second control unit 50 control the liquid delivery operation of the liquid delivery unit 100 so that the scheduled delivery amount of insulin is delivered to the living body.

The first storage unit 262 stores each of the parameters of an insulin to carbohydrate ratio, a target blood glucose level, and an insulin effect value as data necessary for the calculation by the calculation unit 261. These parameters can be input by the user in advance via the reception unit 230 and can be set prior to use.

The first storage unit 262 further stores a plurality of residual amount estimation equations (the above Equation 2) corresponding to the activity amount detected by the activity detection unit 60. Specifically, in the present embodiment, as illustrated in FIG. 6B, the first storage unit 262 stores in advance three residual amount estimation equations, that is, a residual amount estimation equation corresponding to the motion pattern of Act1 in which the activity amount detected by the activity detection unit 60 is A1, a residual amount estimation equation corresponding to the motion pattern of Act2 in which the activity amount is A2, and a residual amount estimation equation corresponding to the motion pattern of Act3 in which the activity amount is A3. Note that, as described above, Act1 corresponds to the motion pattern in the case where the amount of the motion of the user was relatively small since the user had a sleep or a rest, Act2 corresponds to the motion pattern in the case where the user continuously performed daily activities such as walking, and Act3 corresponds to the motion pattern in the case where the user continuously performed a vigorous activity such as exercise. The residual amount estimation equations stored in the first storage unit 262 can be set prior to use by inputting, by the user, a doctor, or the like, data related to metabolism and the like of each user in advance via the reception unit 230.

In a case where there was a liquid delivery instruction in the bolus mode from the user, the calculation unit 261 calculates the residual insulin amount on the basis of the residual amount estimation equation corresponding to the already-delivered liquid data and the activity amount detected by the activity detection unit 60. In the present embodiment, the calculation unit 261 acquires, from the activity amount management unit 52 of the second control unit 50, the integrated activity amount between the completion of the liquid delivery operation in the previous bolus mode by the liquid delivery unit 100 and the start of another liquid delivery operation (liquid delivery in the next bolus mode) (hereinafter referred to as "integrated activity amount"), and the number of integration. The calculation unit 261 then calculates an average activity amount by dividing the integrated activity amount by the number of integration. The calculation unit 261 compares the calculated average activity amount with the activity amounts A1, A2, and A3 in the motion patterns Act1, Act2, and Act3, and selects the residual amount estimation equation corresponding to the nearest activity amount. Next, the calculation unit 261 acquires the already-delivered liquid data from the second storage unit 51 of the second control unit 50. The calculation unit 261 then calculates elapsed time from the liquid delivery end time of the acquired already-delivered liquid data to the next liquid delivery start time. The calculation unit 261 then calculates the residual insulin amount by applying the liquid delivery amount of the already-delivered liquid data and the calculated elapsed time to the selected residual amount estimation equation (Equation 2).

Here, an example of calculation of the residual insulin amount and the scheduled liquid delivery amount will be described with reference to FIGS. 8 and 9 illustrating temporal changes in the delivery amount of insulin, the activity amount, and the residual amount of the liquid medicine in the insulin administration device 300. FIGS. 8A-8C illustrate a case in which the residual amount estimation equation of the motion pattern of Act1 in the case where the amount of the motion of the body is relatively small is selected. FIGS. 9A-9B illustrate a case where the residual amount estimation equation of the motion pattern of Act2 in a case where a moderate activity amount A2 is detected is selected.

First, the case where the residual amount estimation equation corresponding to Act1 in FIG. 8 is selected will be described.

FIG. 8A exemplifies a state in which the liquid delivery in a first bolus mode has been performed between time $t_{0s}$ and time $t_{0f}$, the liquid delivery amount at that time being assumed as $V_0$, thereafter, there was a liquid delivery instruction in the bolus mode from the user, and liquid delivery in a second bolus mode is to be started at time $t_{ns}$.

In the calculation of the residual insulin amount, the calculation unit 261 first calculates, as illustrated in FIG. 8B, an average activity amount Ave1 on the basis of an integrated activity amount $S_1$ and the number of integration between a liquid delivery end time $t_{0f}$ in the first bolus mode and a liquid delivery start time tns in the second bolus mode. The calculation unit 261 then compares the predetermined average activity amounts A1, A2, and A3 stored in the first storage unit 262 with the calculated average activity amount Ave1, and selects the residual amount estimation equation corresponding to the predetermined average activity amount nearest to the calculated average activity amount Ave1. As illustrated in FIG. 8C, the residual amount estimation equation corresponding to the motion pattern Act1 is selected, and the residual insulin amount after the lapse of Δt from the first liquid delivery end time $t_{0f}$ (at time $t_{ns}$) is calculated as $V_1$.

The calculation unit 261 calculates a scheduled liquid delivery amount $V_{n1}$ in the second bolus mode by applying a residual insulin amount $V_1$ to the above Equation 1. The liquid delivery unit 100 then performs liquid delivery of the calculated scheduled liquid delivery amount $V_{n1}$. As illustrated in FIG. 8C, an insulin amount $V_{n1}$ administered in the second bolus mode is added to the residual insulin amount $V_1$ at the second liquid delivery start time $t_{ns}$, and as a result, $V_p$ of insulin in total exists in the living body at a second liquid delivery end time $t_{nf}$.

Next, a case where the residual amount estimation equation corresponding to Act2 in FIGS. 9A-9C is selected will be described.

In the calculation of the residual insulin amount, the calculation unit 261 first calculates, as illustrated in FIG. 9B, an average activity amount Ave2 from an integrated activity amount $S_2$ and the number of integration between the liquid delivery end time $t_{0f}$ in the first bolus mode and the liquid delivery start time $t_{ns}$ in the second bolus mode. The calculation unit 261 then compares the predetermined average activity amounts A1, A2, and A3 stored in the first storage unit 262 with the calculated average activity amount Ave2, and selects the residual amount estimation equation corresponding to the predetermined average activity amount nearest to the calculated average activity amount Ave2. As illustrated in FIG. 9C, the residual amount estimation equation of the motion pattern Act2 is selected, and when the liquid delivery amount in the first bolus mode is $V_0$, the residual insulin amount after the lapse of Δt from the first liquid delivery end time $t_{0f}$ (at time $t_{ns}$) is calculated as $V_2$.

The calculation unit 261 calculates a scheduled liquid delivery amount $V_{n2}$ in the second bolus mode by applying a residual insulin amount $V_2$ to the above Equation 1. The liquid delivery unit 100 then performs liquid delivery of the calculated scheduled liquid delivery amount $V_{n2}$. As illustrated in FIG. 9C, an insulin amount $V_{n2}$ administered in the second bolus mode is added to the residual insulin amount $V_2$ at the second liquid delivery start time $t_{ns}$, and as a result, $V_p$ of insulin in total exists in the living body at the second liquid delivery end time $t_{nf}$.

As described above, in both cases of FIGS. 8 and 9, $V_p$ of insulin in total exists in the living body as a result at the liquid delivery end time $t_{nf}$ in the second bolus mode. In this way, by the calculation of the residual insulin amount taking the activity amount into consideration, an appropriate amount of insulin can be administered. Note that, also in a case where the residual amount estimation equation corresponding to Act3 is selected, the calculation is performed in a similar way.

Next, an example of operation processes of the insulin administration device 300 will be described with reference to FIGS. 10 and 11.

First, operation processes of the first control unit 260 provided in the controller 200 will be described.

As illustrated in FIG. 10, when a liquid delivery instruction in the bolus mode is received from the user via the reception unit 230, the first control unit 260 provided in the controller 200 instructs the user via the display unit 220 to input the amount of carbohydrate (S11). The user who received the instruction inputs the amount of carbohydrate obtained from contents of a meal taken immediately before via an input button of the reception unit 230.

Next, the first control unit 260 instructs the user via the display unit 220 to input the measured blood glucose level (S12). The user who received the instruction inputs the blood glucose level before taking a meal measured using a known blood glucose level measuring device or the like via the input button of the reception unit 230.

Next, the first control unit 260 requests the activity amount management unit 52 of the second control unit 50 provided in the liquid delivery unit 100 to send the activity amount (the integrated activity amount and the number of integration) (S13), using a wireless communication function of the first communication unit 250. The first control unit 260 then receives, in the first communication unit 250, the integrated activity amount and the number of integration sent by the activity amount management unit 52 in response to the request.

Next, the calculation unit 261 selects the residual amount estimation equation (S14). Specifically, first, the calculation unit 261 calculates the average activity amount from the integrated activity amount and the number of integration received in step (S13). The calculated average activity amount is compared with the predetermined activity amounts A1, A2, and A3 corresponding to motion patterns stored in the first storage unit 262, and the residual amount estimation equation corresponding to the motion pattern of the activity amount a value of which is nearest to the calculated average activity amount is selected.

Next, the first control unit 260 requests the already-delivered liquid data to the second storage unit 51 of the second control unit 50 provided in the liquid delivery unit 100 using the wireless communication function of the first communication unit 250 (S15). The first control unit 260 then receives, in the first communication unit 250, the already-delivered liquid data sent from the second storage unit 51 in response to the request.

Next, on the basis of the residual amount estimation equation selected in step (S14) and the already-delivered liquid data received in step (S15), the calculation unit 261 calculates the residual insulin amount (S16). Specifically, the calculation unit 261 calculates the elapsed time from the liquid delivery end time of the already-delivered liquid data received in step (S15) to the liquid delivery start time in the next bolus mode. Then, the liquid delivery amount of the already-delivered liquid data and the calculated elapsed time are applied to the residual amount estimation equation selected in step (S14), and calculated.

Next, the calculation unit 261 acquires the insulin to carbohydrate ratio, the insulin effect value, and the target blood glucose level from the first storage unit 262 (S17).

Next, the calculation unit 261 calculates the scheduled liquid delivery amount (S18) by applying, to Equation 1, the amount of carbohydrate and the measured blood glucose level input in step (S11) and step (S12), the residual insulin amount calculated in step (S16), and the insulin to carbohydrate ratio, the insulin effect value, and the target blood glucose level acquired in step (S17).

Next, the first control unit 260 sends, using the wireless communication function of the first communication unit 250, a liquid delivery instruction to the liquid delivery unit 100 to deliver the scheduled delivery amount of insulin in the bolus mode (S19). After completion of the operation process in step (S18), the first control unit 260 stands by until receiving an instruction from the user again.

The above is the operation processes in a case where the controller 200 receives a liquid delivery instruction in the bolus mode from the user.

Next, operation processes of the second control unit 50 provided in the liquid delivery unit 100 will be described.

As illustrated in FIG. 11, when starting to use the liquid delivery unit 100, the activity amount management unit 52 of the second control unit 50 acquires the activity amount from the activity detection unit 60, and adds the acquired new activity amount to a previous activity amount to obtain the integrated activity amount (S21). At the same time, the number of integration, which is the number of times the activity amount is added, is counted. Note that the integration of the activity amount and the count of the number of integration are periodically performed during subsequent operation processes. Further, the acquired integrated activity amount and the acquired number of integration are reset (set to 0) when the operation process proceeds to step (S43) to be described later.

Subsequently, the second control unit 50 determines whether or not a signal sent from the controller 200 is received (S22).

In a case where it is determined in step (S22) that the signal sent from the controller 200 is not received (S22; No), the second control unit 50 continues to perform a series of processes from step (S21).

In a case where it is determined in step (S22) that the signal sent from the controller 200 is received (S22; Yes), the second control unit 50 determines whether or not the signal requests the activity amount (the integrated activity amount and the number of integration) or the already-delivered liquid data (S23).

In a case where it is determined in step (S23) that the signal from the controller 200 requests the activity amount (the integrated activity amount and the number of integration) and the already-delivered liquid data (S23: Yes), the second control unit 50 sends the requested information from the second communication unit 40 (S24).

After completion of the operation in step (S24), the second control unit 50 performs a series of processes from step (S21) again.

In a case where it is determined in step (S23) that the signal from the controller 200 does not require the integrated activity amount and the number of integration, or the already-delivered liquid data (S23; No), the second control unit 50 determines whether or not the signal is an instruction signal to perform liquid delivery in the basal mode (S31).

In a case where it is determined in step (S31) that the signal from the controller 200 is the instruction signal to perform liquid delivery in the basal mode (S31; Yes), the second control unit 50 electrically controls the motor 32 to perform the liquid delivery in the basal mode (S32).

After completion of the operation in step (S32), the second control unit 50 continues to perform a series of processes from step (S21).

In a case where it is determined in step (S31) that the signal from the controller 200 is not the instruction signal to perform liquid delivery in the basal mode (S31; No), the second control unit 50 determines whether or not the signal is an instruction signal to perform liquid delivery in the bolus mode (S41).

In a case where it is determined in step (S41) that the signal from the controller 200 is the instruction signal to perform liquid delivery in the bolus mode (S41; Yes), the second control unit 50 electrically controls the motor 32 of the liquid delivery unit 100 so that the scheduled delivery amount of insulin is delivered to perform the liquid delivery in the bolus mode (S42). At this time, the second control unit 50 acquires, from the drive signal of the motor 32, the already-delivered liquid data including the liquid delivery amount and the liquid delivery end time that are sent by the liquid delivery unit 100.

After completion of the operation in step (S42), the activity amount management unit 52 of the second control unit 50 resets values of the integrated activity amount and the number of integration, and the second storage unit 51 of the second control unit 50 updates the acquired liquid delivery amount and the liquid delivery end time in step (S42) as the already-delivered liquid data (S43).

After completion of the operation in step (S43), the second control unit 50 performs a series of processes from step (S21) again.

Note that, in a case where it is determined in step (S41) that the signal received from the controller 200 is not the instruction signal to perform liquid delivery in the bolus mode, the second control unit 50 sends an error signal indicating that the signal is not normally received to the first control unit 260 provided in the controller 200 (S44).

After completion of the operation in step (S44), the second control unit 50 performs a series of operation processes from step (S21) again.

The above is an example of the operation processes of the second control unit 50.

As described above, the insulin administration device 300 according to the present embodiment can calculate the scheduled liquid delivery amount using the residual amount of the liquid medicine in the living body calculated in consideration of the activity of the user, and administer an appropriate amount of the liquid medicine into the living body of the user.

The insulin administration device 300 according to the above embodiment administers the liquid medicine in a state where the device is attached to the body of the user, the device including the liquid delivery unit 100 that delivers the liquid medicine into the living body, the first control unit 260 and the second control unit 50 that controls the liquid delivery operation of the liquid delivery unit 100, and the activity detection unit 60 that detects the activity based on the motion of the body of the user. Further, the insulin administration device 300 includes the second storage unit 51 that stores the already-delivered liquid data relating to the delivery amount of the liquid medicine delivered by the liquid delivery unit 100 into the living body, and the calculation unit 261 that calculates the residual amount of the liquid medicine in the living body on the basis of the already-delivered liquid data stored by the second storage unit 51 and the activity detected by the activity detection unit 60, and calculates the scheduled delivery amount of the liquid medicine to be administered into the living body on the basis of the residual amount of the liquid medicine. In addition, the first control unit 260 and the second control unit 50 control the liquid delivery operation of the liquid delivery unit 100 so that the scheduled delivery amount of the liquid medicine is delivered into the living body. Thus it is possible to calculate an appropriate dosage of the liquid medicine on the basis of the residual amount of the liquid medicine in the living body calculated in consideration of the activity of the user. As a result, a more appropriate amount of the liquid medicine can be administered into the living body of the user.

Further, in the insulin administration device 300 according to the above embodiment, the first storage unit 262 stores the residual amount estimation equation that calculates the residual amount of the liquid medicine on the basis of the already-delivered liquid data and the activity, and the calculation unit 261 calculates the residual amount of the liquid medicine on the basis of the residual amount estimation equation stored by the first storage unit 262. Thus the residual amount of the liquid medicine can be calculated easily and efficiently using the residual amount estimation equation.

Further, in the insulin administration device 300 according to the above embodiment, the first storage unit 262 stores a plurality of residual amount estimation equations corresponding to the activities detected by the activity detection unit 60, and the calculation unit 261 calculates the residual amount of the liquid medicine on the basis of the residual amount estimation equation corresponding to the activities detected by the activity detection unit 60. Thus an optimum residual amount estimation equation can be selected from the residual amount estimation equations corresponding to a plurality of predetermined activities stored in advance, and therefore, it is possible to deal with various motion patterns of the user (sleep, daily activities, exercise, and the like).

Further, in the insulin administration device 300 according to the above embodiment, the calculation unit 261 calculates the residual amount of the liquid medicine on the basis of the already-delivered liquid data and the activity between the completion of the liquid delivery operation of the liquid delivery unit 100 and the start of another liquid delivery operation. Thus an appropriate residual amount of the liquid medicine based on the activity between the previous liquid delivery and the start of the next liquid delivery can be calculated.

Further, in the insulin administration device 300 according to the above embodiment, the liquid delivery unit 100 is configured to be capable of performing the liquid delivery operation in the bolus mode in which the delivery amount of insulin per unit time is temporarily increased to perform the liquid delivery, in contrast to the basal mode in which insulin as the liquid medicine is continuously delivered in a fixed amount, and the calculation unit 261 calculates the residual amount and the scheduled delivery amount of the liquid medicine in the bolus mode. Thus an appropriate amount of insulin can be administered in the liquid delivery in the bolus mode in which dosage is large.

Although embodiments of the liquid medicine administration device have been described above, the liquid medicine administration device according to the present invention is not limited to the described embodiments, and various modifications can be made while remaining in the scope of the invention.

For example, in the liquid medicine administration device 300 according to an embodiment described above, insulin is used as a liquid medicine to be delivered, but the present invention is not limited to the use of insulin. The liquid medicine is not limited to insulin, and the liquid medicine administration device 300 can also be used for administration of a liquid medicine such as insulin, antibiotics, nutrients, analgesics, hormones, or the like. The method of calculating the residual amount of the liquid medicine in the living body and the scheduled liquid delivery amount can be appropriately changed in accordance with a kind and an administration method of the liquid medicine.

Further, for example, the liquid medicine administration device 300 according to an embodiment described above includes the liquid delivery unit 100 and the controller 200 separate from the liquid delivery unit 100, but the present invention is not limited to this configuration. For example, it is possible to integrate functions of the controller 200 into the liquid delivery unit 100 so that the liquid medicine administration device 300 has an integrated configuration.

Further, for example, in the liquid medicine administration device 300 according to an embodiment described above, the liquid delivery unit 100 is configured by combining the injection unit 10, the liquid delivery disposable unit 20, and the liquid delivery reusable unit 30, but the present invention is not limited to this configuration. For example, the injection unit 10, the liquid delivery disposable unit 20, and the liquid delivery reusable unit 30 may be integrated.

Further, for example, in the liquid medicine administration device 300 according to an embodiment described above, a drive mechanism including the motor 32, the feed screw 25, and the like is adopted as drive means that delivers the liquid medicine, but the present invention is not limited to this configuration. For example, a pump or the like can also be used as the drive means.

Further, for example, the liquid medicine administration device 300 according to an embodiment described above includes the first control unit 260 and the second control unit 50, but the present invention is not limited to this configuration. For example, when the liquid medicine administration device 300 does not include a controller, it is also possible to provide only one control unit.

Further, for example, in the liquid medicine administration device 300 according to an embodiment described above, it is assumed that the liquid medicine (insulin) administered in the living body decreases at a constant rate with respect to the elapsed time. However, it is also possible to calculate the residual amount of the liquid medicine assuming that a reduction rate of the liquid medicine changes over time, for example.

Further, for example, in the liquid medicine administration device 300 according to an embodiment described above, the already-delivered liquid data is the amount of the delivered liquid medicine in the living body and the liquid delivery end time, but the present invention is not limited to this configuration. For example, in a case where the administration of the liquid medicine is performed at predetermined time intervals, the already-delivered liquid data may be only the amount of the delivered liquid medicine.

Further, for example, in the liquid medicine administration device 300 according to an embodiment described above, the activity of the user is considered only in the calculation of the residual insulin amount, but the present invention is not limited to this configuration. For example, not only the residual insulin amount but also the insulin to carbohydrate ratio and the insulin effect value in the above Equation 1 can be set to values in consideration of the activity of the user.

Further, for example, in the liquid medicine administration device 300 according to an embodiment described above, the first storage unit 262 is configured to store three residual estimation equations, but the number of residual estimation equations to be stored is not limited to three. The number of residual amount estimation equations to be stored can be appropriately set according to storage capacity of a storage unit.

Further, for example, in the liquid medicine administration device 300 according to an embodiment described above, the residual insulin amount is calculated on the basis of the average activity amount calculated from the integrated activity amount and the number of integration, but the present invention is not limited to this configuration, and the configuration may be appropriately changed. For example, the residual insulin amount may be calculated on the basis of the activity amount per unit time calculated by dividing the integrated activity amount by elapsed time from the previous bolus to the current bolus, instead of dividing the integrated activity amount by the number of integration.

Further, for example, in the liquid medicine administration device 300 according to an embodiment described above, the first storage unit 262 stores the residual amount estimation equation in which the consumption of insulin is promoted and the decreasing rate of the residual insulin amount becomes higher as the amount of the activity of the user increases, but the present invention is not limited to this configuration. For example, the first storage unit 262 may store a residual amount estimation equation in which the consumption of insulin is suppressed and the decreasing rate of the residual insulin amount becomes lower as the amount of the activity of the user increases.

Further, for example, in the liquid medicine administration device 300 according to an embodiment described above, the liquid delivery end time is used as the already-delivered liquid data, but the already-delivered liquid data is not limited to liquid delivery end time. It is also possible to select the liquid delivery start time or an intermediate time between the liquid delivery start time and the liquid delivery end time, for example.

Further, for example, in the liquid medicine administration device 300 according to an embodiment described above, the liquid delivery amount of the already-delivered liquid data and the liquid delivery end time are acquired from the drive signal of the motor 32 provided in the liquid delivery unit 100, but the present invention is not limited to this configuration. For example, the liquid delivery amount and timing instructed by the controller 200 can be treated as the previous bolus data.

The present application is based on Japanese Patent Application No. 2015-067113 filed on Mar. 26, 2015, the disclosure of which is incorporated by reference in its entirety.

REFERENCE NUMERAL LIST

10 Injection unit
11 Cannula
15 Puncture tool
20 Liquid delivery disposable unit
22 Syringe
24 Pusher
25 Feed screw
30 Liquid delivery reusable unit
35 Drive unit
40 Second communication unit
50 Second control unit
51 Second storage unit
52 Activity amount management unit
60 Activity detection unit
100 Liquid delivery unit
200 Controller
220 Display unit
230 Reception unit
250 First communication unit
260 First control unit
261 Calculation unit
262 First storage unit
300 Insulin administration device

What is claimed is:

1. A liquid medicine administration device for administration of a liquid medicine in a state in which the device is attached to a body of a user, the device comprising:
a liquid delivery unit configured to deliver the liquid medicine into a living body of the user and to perform a liquid delivery operation in (i) a bolus mode in which the delivery amount of insulin per unit time is temporarily increased, and (ii) a basal mode in which insulin as the liquid medicine is continuously delivered in a fixed amount;
a control unit configured to control the liquid delivery operation of the liquid delivery unit;
an activity detection unit configured to detect an activity of the user based on a motion of the body of the user;
a storage unit configured to store data indicating an amount of the liquid medicine that has already been delivered by the liquid delivery unit into the living body and configured to store at least one residual amount estimation equation; and
a calculation unit configured to, in the bolus mode:
calculate a residual amount of the liquid medicine in the living body on the basis of (i) the data indicating the amount of the liquid medicine that has already been delivered by the liquid delivery unit into the living body in a previous bolus, (ii) the activity of the user detected by the activity detection unit after the previous bolus, and (iii) an elapsed time from the previous bolus, using the at least one residual amount estimation equation, and
calculate a scheduled delivery amount of the liquid medicine to be administered into the living body on the basis of the residual amount of the liquid medicine,
wherein the control unit is configured to control the liquid delivery operation of the liquid delivery unit such that the scheduled delivery amount of the liquid medicine is delivered to the living body.

2. The liquid medicine administration device according to claim 1, wherein
the at least one residual amount estimation equations comprises a plurality of residual amount estimation equations each corresponding to a different activity of the user, and
the calculation unit is configured to calculate the residual amount of the liquid medicine on the basis of a residual amount estimation equation corresponding to the activity detected by the activity detection unit.

3. A liquid medicine administration device for administration of a liquid medicine in a state in which the device is attached to a body of a user, the device comprising:
a liquid delivery unit configured to deliver the liquid medicine into a living body of the user and to perform a liquid delivery operation in (i) a bolus mode in which the delivery amount of insulin per unit time is temporarily increased, and (ii) a basal mode in which insulin as the liquid medicine is continuously delivered in a fixed amount;
an activity detection unit configured to detect an activity of the user based on a motion of the body of the user;
at least one control unit configured to:
control the liquid delivery operation of the liquid delivery unit,
store data indicating an amount of the liquid medicine that has already been delivered by the liquid delivery unit into the living body and store at least one residual amount estimation equation,
calculate a residual amount of the liquid medicine in the living body, in the bolus mode, on the basis of (i) the data indicating the amount of the liquid medicine that has already been delivered by the liquid delivery unit into the living body in a previous bolus, (ii) the activity of the user detected by the activity detection unit after the previous bolus, and (iii) an elapsed time from the previous bolus, using the at least one residual amount estimation equation,
calculate a scheduled delivery amount of the liquid medicine to be administered into the living body on the basis of the residual amount of the liquid medicine, and
control the liquid delivery operation of the liquid delivery unit such that the scheduled delivery amount of the liquid medicine is delivered to the living body.

4. A method of administering a liquid medicine, the method comprising:
providing an administration device configured to be attached to a body of a user, the device comprising:
a liquid delivery unit configured to deliver the liquid medicine into a living body of the user and to perform a liquid delivery operation in (i) a bolus mode in which the delivery amount of insulin per unit time is temporarily increased, and (ii) a basal mode in which insulin as the liquid medicine is continuously delivered in a fixed amount;
an activity detection unit configured to detect an activity of the user based on a motion of the body of the user; and
at least one control unit;
using the at least one control unit, storing data indicating an amount of the liquid medicine that has already been delivered by the liquid delivery unit into the living body, and storing at least one residual amount estimation equation;

using the at least one control unit, calculating a residual amount of the liquid medicine in the living body, in the bolus mode, on the basis of (i) the data indicating the amount of the liquid medicine that has already been delivered by the liquid delivery unit into the living body in a previous bolus, (ii) the activity of the user detected by the activity detection unit after the previous bolus, and (iii) an elapsed time from the previous bolus, using the at least one residual amount estimation equation;

using the at least one control unit, calculating a scheduled delivery amount of the liquid medicine to be administered into the living body on the basis of the residual amount of the liquid medicine; and using the at least one control unit, controlling the liquid delivery operation of the liquid delivery unit such that the scheduled delivery amount of the liquid medicine is delivered to the living body.

* * * * *